United States Patent
Preston

[19]

[11] Patent Number: 6,035,727

[45] Date of Patent: Mar. 14, 2000

[54] REMOTE CONTROL SAMPLER FOR GRAIN STORAGE BINS

[76] Inventor: Richard Charles Preston, P.O. Box 41, Brock, Saskatchewan, Brock Sask, Canada, S0L 0H0

[21] Appl. No.: 08/960,069

[22] Filed: Oct. 29, 1997

[30] Foreign Application Priority Data

Mar. 11, 1997 [CA] Canada ................................... 2198398

[51] Int. Cl.[7] .................................................. G01N 1/12
[52] U.S. Cl. .................................... 73/864.64; 73/864.63; 73/863.33; 73/863.86
[58] Field of Search ........................... 73/863.33, 863.41, 73/863.57, 863.86, 864.63, 864.64

[56] References Cited

U.S. PATENT DOCUMENTS

| | | | |
|---|---|---|---|
| 185,024 | 12/1876 | Gent ...................................... | 73/864.64 |
| 840,943 | 1/1907 | Ingold .................................... | 73/863.33 |
| 1,966,712 | 7/1934 | Fisher et al. ...................... | 73/863.86 X |
| 2,516,097 | 7/1950 | Woodham et al. .............. | 73/864.64 X |
| 2,875,615 | 3/1959 | Ulvin .................................... | 73/863.33 |
| 3,675,491 | 7/1972 | Guillet ................................. | 73/864.63 |
| 4,838,094 | 6/1989 | Baldock ........................... | 73/864.64 X |
| 5,567,888 | 10/1996 | Boydle et al. ....................... | 73/863.86 |

*Primary Examiner*—Daniel S. Larkin

[57] ABSTRACT

A remotely controllable grain sampling device mounted on the vertical outer wall of a grain storage bin and extending into the interior of the bin so as to extract a sample of grain to be tested, for example, for moisture content, protein content or disease. The sampler is an inclined tube having an opening and closing device on the inner end of the tube that is operated by movement of an internal push rod that may be caused to move by the pull of a rope or cable from a convenient location. The grain sample is collected at a site convenient to the operator.

9 Claims, 5 Drawing Sheets

REMOTE CONTROL SAMPLER FOR GRAIN STORAGE BINS

CROSS-REFERENCE TO RELATED APPLICATION

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

The invention relates to a remotely controllable grain sampling device.

Previously, sampling of grain from storage bins often involved the farmer having to climb to an unsafe height so as to obtain a grain sample from the upper levels of grain in a storage bin. The sampler often consisted of a portable probe of some length. The probe was awkward and dangerous to operate on the top of high storage bins.

Previous samplers mounted inside storage bins, in many cases could not withstand the great pressure exerted on them by the rapid removal of grain from the storage bin.

Prior samplers were subject to dirt and small granules entering between moving surfaces causing them to be difficult to operate.

A common present-day agricultural practice is to harvest grain early in the season. Harvested grains are at a higher moisture content than is safe for long-term storage of the grain. Farmers put their grain into a grain storage bin equipped with a motor-driven fan which blows air through the grain in the storage bin causing the grain to dry down to a moisture level that is safe for storage of the grain for extended periods of time.

Typical aeration storage bins have the fan at the lower portion of the storage bin. It is important to the farmer to be aware of the progression of drying as the drying process travels upward from the lower portion of the storage bin to the upper portion thereof. Until the present time, a practical method of determining the condition of grain at various levels in the storage bin was unavailable.

BRIEF SUMMARY OF THE INVENTION

This invention is a grain sampler that can be permanently mounted on the high outer wall of a grain storage bin and may be operated by the user from a safe position on the ground.

The sampler consist of a steeply inclined tube having a valve on the inner upper end that is opened to allow the flow of grain. The valve is opened by pulling a rope which forces a rod connected to the valve to move inward.

The valve is closed by relaxing the rope thereby causing a compression spring to force the rod and valve outward thus shutting off the flow of grain.

Moving parts have sufficient clearance so as to prevent fine granules from aversely affecting the devices operation.

Saving of energy and therefore money is accomplished as the farmer using the invention will know when the grain is dry enough to permit the aeration fan to be shut off.

DETAILED DESCRIPTION OF THE INVENTION

Figure 1:
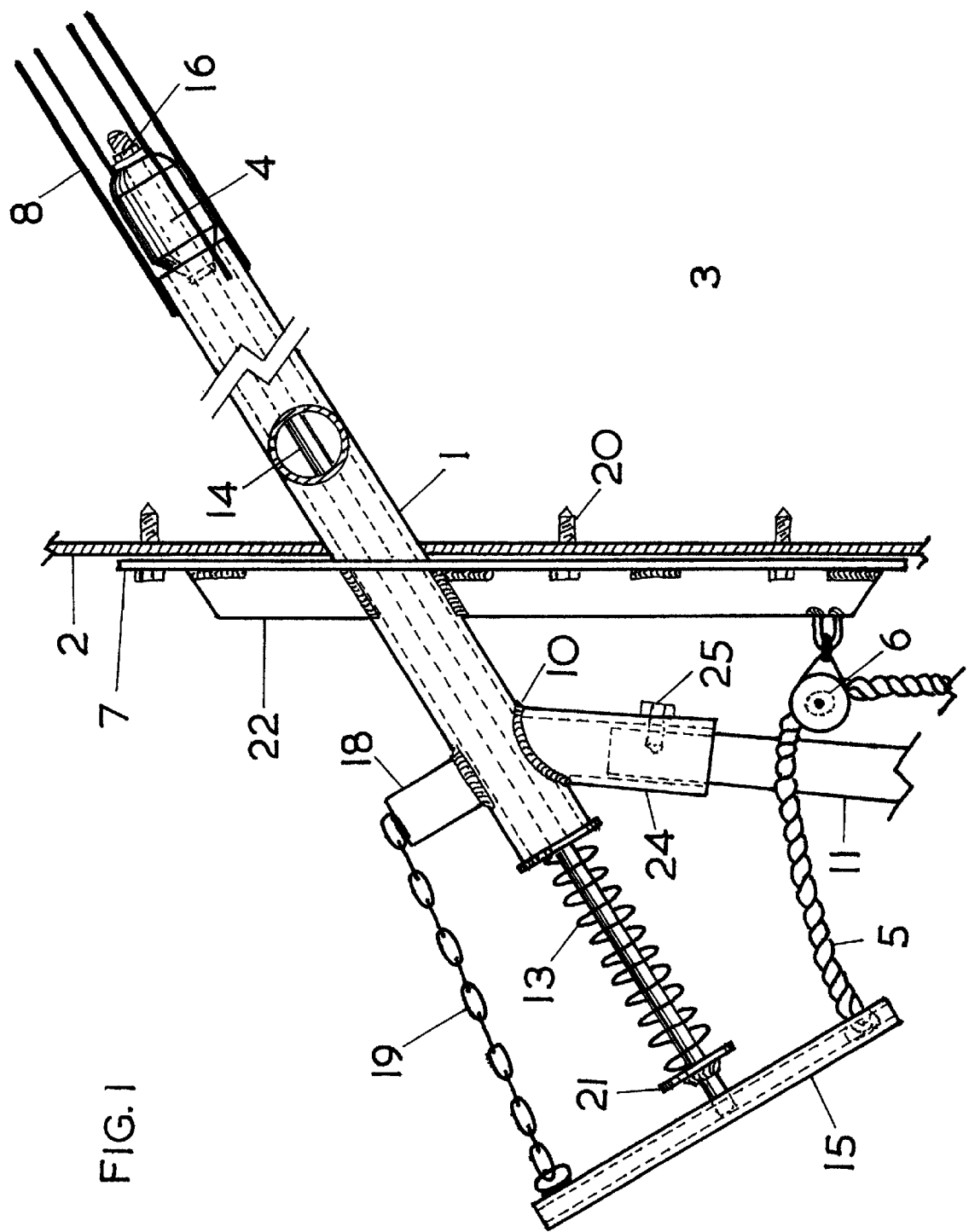
FIG.1 is a side view of a grain sampling device depicting a closed valve position.

Referring now to the drawings, wherein like reference numerals designate like or corresponding elements throughout the views and particularly referring to FIG. 1, there is shown the grain sampling device comprising the invention.

The grain sampling device consists of a tube 1 extending from outside the vertical wall 2 of a grain storage bin to the interior of the storage bin 3. The tube 1 is steeply inclined having the lower end outside the storage bin wall 2 and the inner end containing a valve 4 being the uppermost end of the device.

Figure 2:
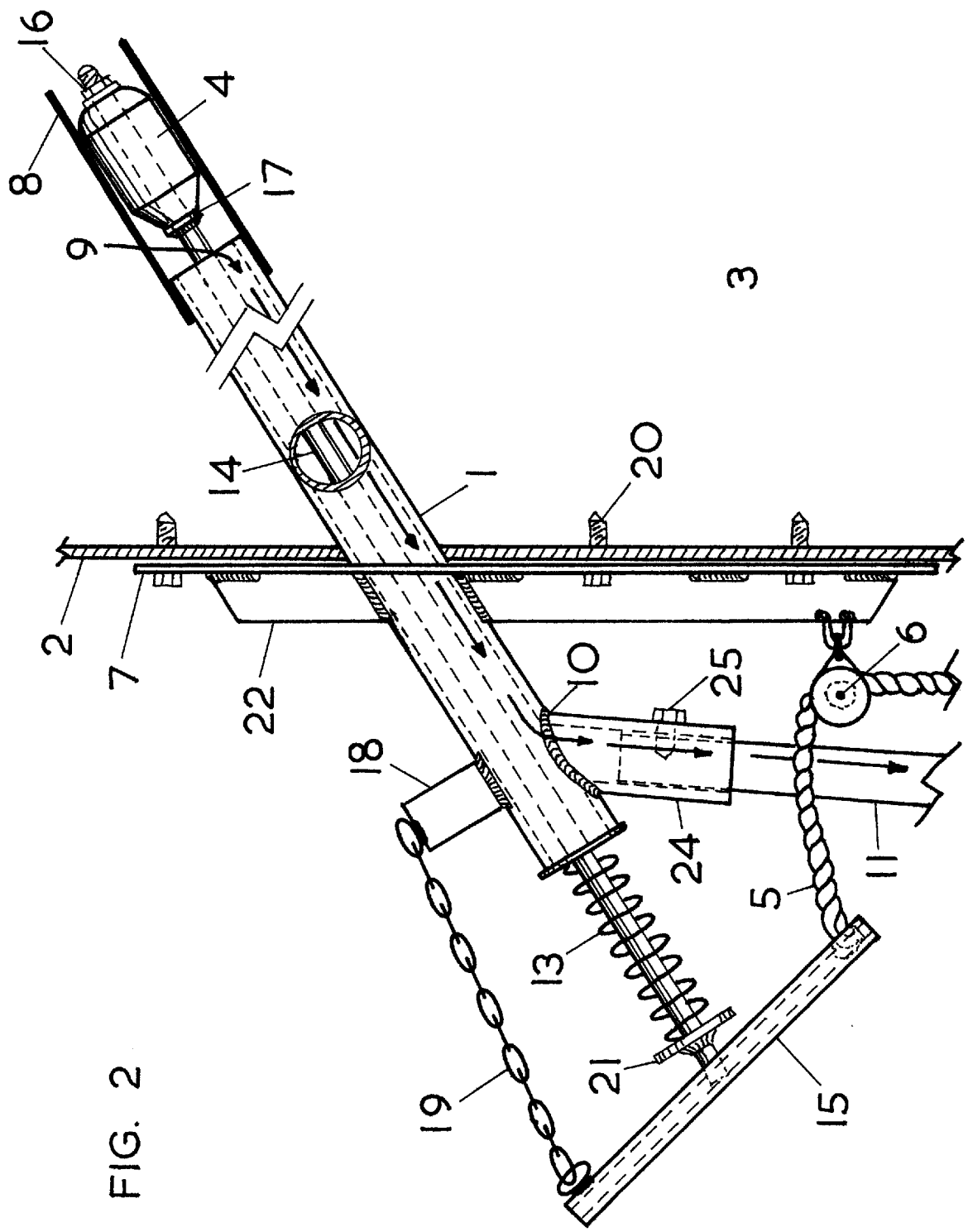
FIG.2 is a side view of a grain sampling device depicting an open valve position and grain movement through the device.
Figure 3:
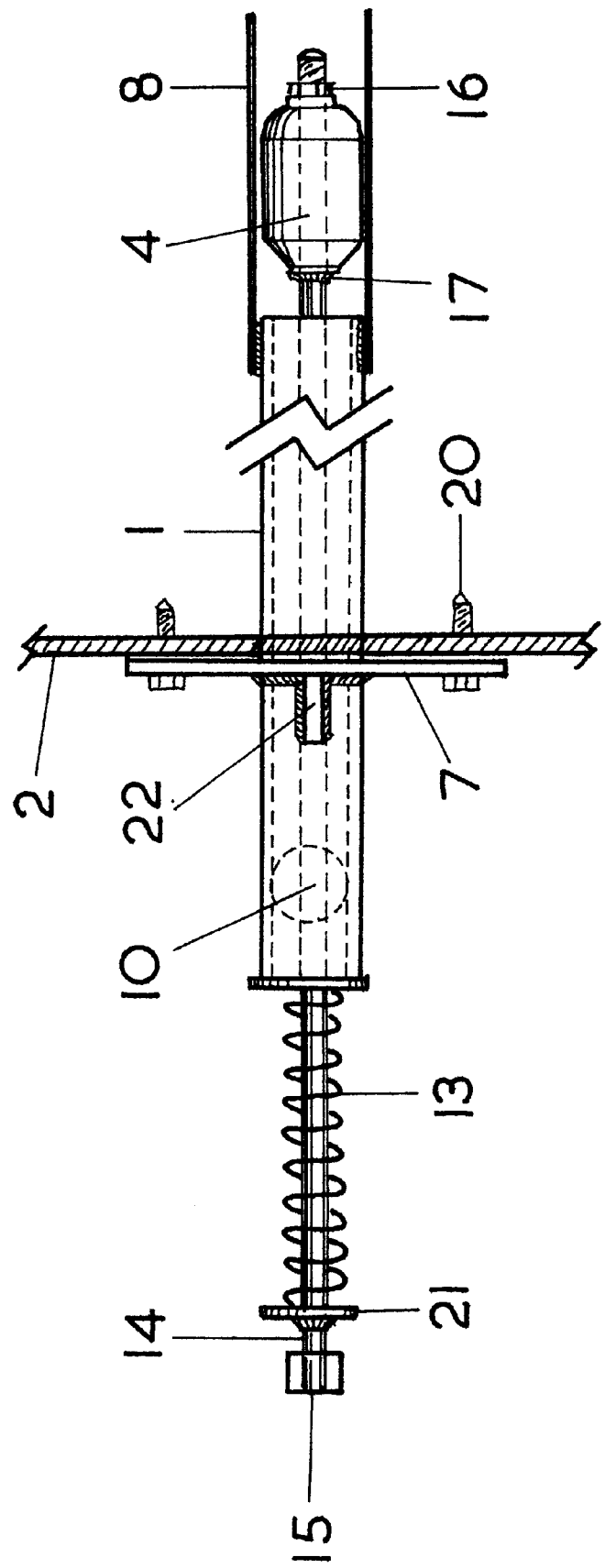
FIG.3 is a top view of the sampler. The chain portion of the sampler is not shown in this view.

Referring now to FIG. 2, the valve 4, is opened by remote control as by the pull of a rope 5. The rope runs through a pulley block 6, that is fastened by welding to the strengthening plate 22. The valve guide pins 8 align the valve 4 with the center of the tube 1 when the valve 4 is in the open position.

When the valve 4 has been opened, grain flows 9 by gravity down the inclined tube 1 to the opening 10 near the lower end of the tube 1. The grain falls through the opening 10. The grain flows 9 down a sample collecting tube 11 to a sample collection site 12 shown in FIG. 5.

Releasing the rope 5 causes the compression spring 13 to close the valve 4, thereby shutting off the flow of grain.

For clearer viewing only two of the four valve guide pins 8 are shown.

Figure 5:
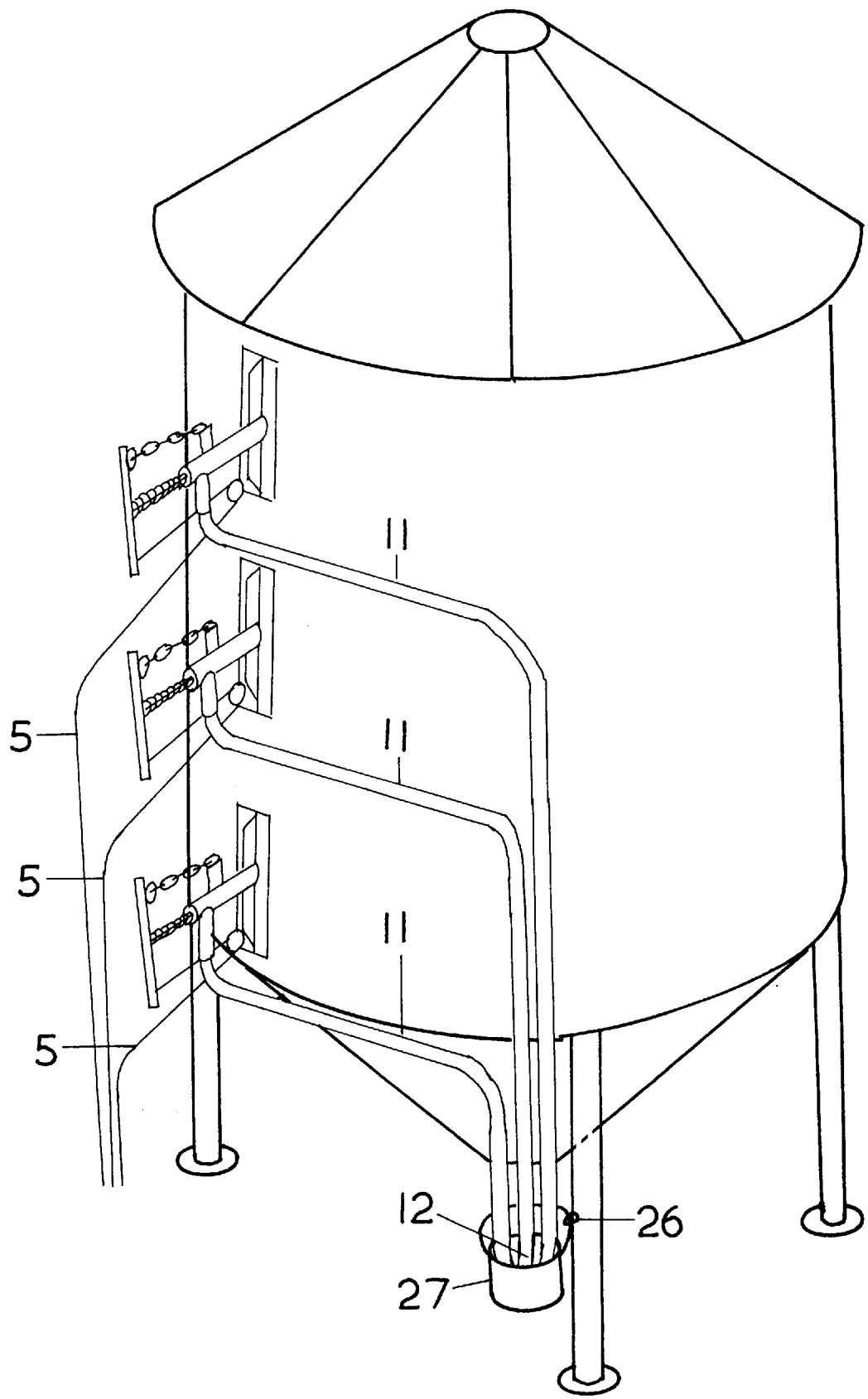
FIG.5 is intended to be a perspective view of a multitude of grain sampling devices mounted on a grain storage bin depicting the use of the sample collecting tubes and the ropes for remote sampling.

Referring now to FIG. 5, depicted in the drawing are a multitude of grain sampling devices mounted at different levels on the vertical bin wall 2. The grain sampling devices each utilize sample collection tubes 11 converging at the sample collection site 12. Also shown are the ropes 5 used to control flow of grain from each sampling device. A sample collection container 27 is shown hanging from a hook 26 at the outlet end of sample collection tubes 11. As is evident to a skilled operator, separate samples can be obtained from different levels in the storage bin and examined separately or combined. So as to be easily understood, the routing of the ropes 5 and the sample collection tubes 11 are shown as being separated. These ropes 5 and tubes 11 would normally be neatly vertical.

As it is evident to those skilled in the art, if the sampler is mounted within reach of the operator, a spring to provide a force to close the valve is not required as an operator can operate the pushrod and valve assembly by direct manual contact.

A more detailed description so as to aid in manufacturing of the device follows: The tube 1 contains a push rod 14 connecting the valve 4 to the lever 15. The push rod 14 extends through the valve 4. The valve 4 is affixed to the push rod 14 by a nut 16 on a threaded portion of the push rod 14. A washer 17 is welded to the push rod 14, thereby enabling the nut 16 to tighten against the valve 4, thus securing the valve 4 to the push rod 14. The push rod 14 extends through a compression spring 13. The compression spring 13 provides a force to close the valve 4 when pressure is released from the lever 15. A flat bar 18 is welded perpendicular to the portion of the tube 1 that is outside the storage bin. The end of a chain 19 is fastened by welding to the top of the flat bar 18. The other end of the chain 19 is affixed to the lever 15 by welding. A mounting plate 7 is fastened to the outside of the storage bin wall 2 by means of screws or bolts 20. A washer 21 is welded to the pushrod 14, thereby enabling the lever 15 to compress the spring 13 and in turn open the valve 4. A strengthening plate 22 is welded to the mounting plate 7 and also to the tube 1. The strengthening plate 22 forms a ninety degree angle with the mounting plate 7. The lower end of the tube 1 is closed by welding, except for a central hole that is large enough to permit in or out movement of the push rod 14.

The valve guide pins 8 are welded to the tube 1. A section of pipe 24 is welded somewhat perpendicular to the tube 1. The sample collection tube 11 enters the pipe 24 and is attached by means of a screw 25 to the pipe 24. The tube 1 is welded to the mounting plate 7.

Figure 4:
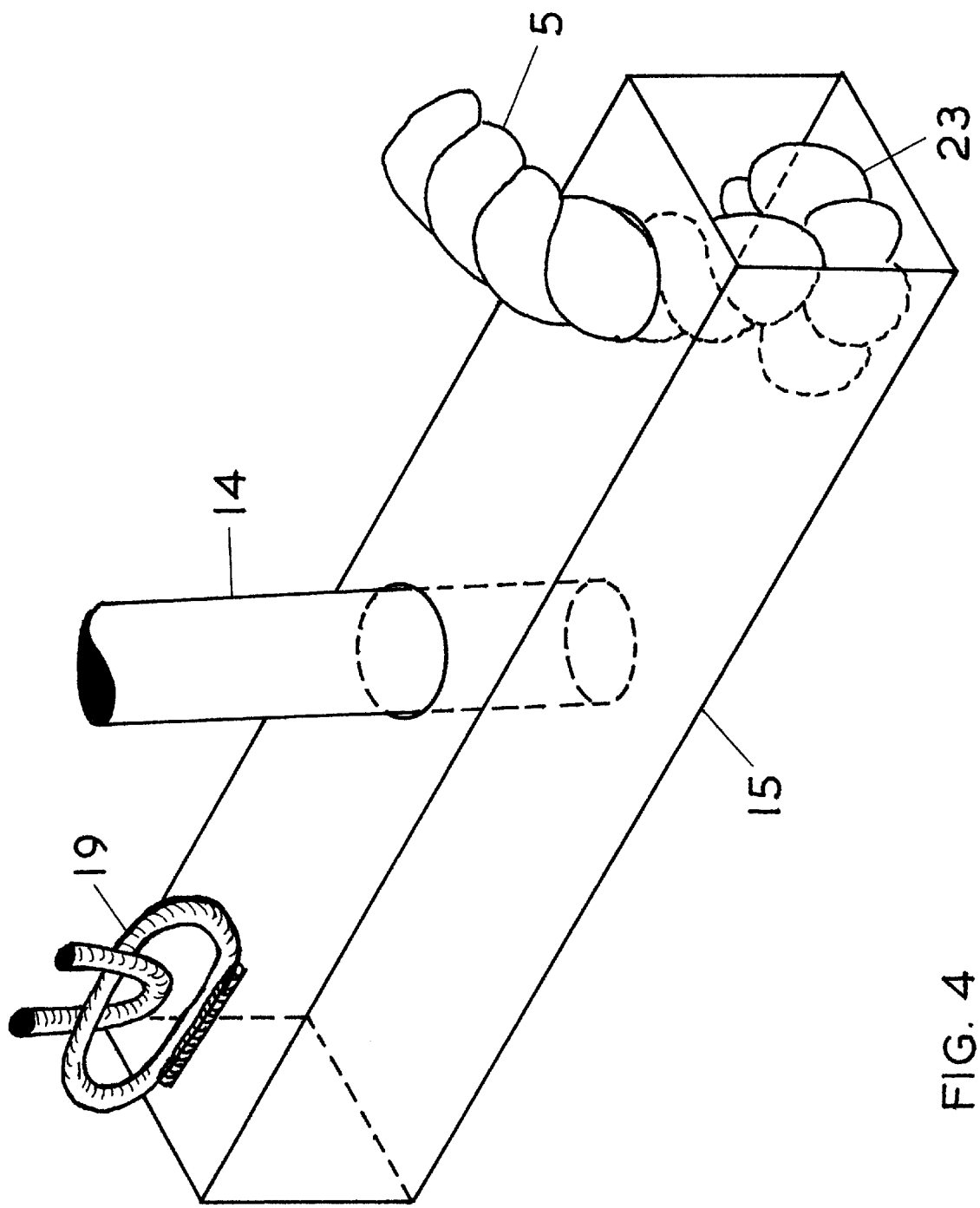
FIG.4 is an enlarged view intended as an aid in manufacturing of the lever.

FIG. 4 is intended to aid in construction of lever 15. The chain 19 is attached to the lever 15 by welding. The push rod 14 protrudes through a hole in one surface of the lever 15. The rope 5 passes through a hole near the end of the lever 15 and out the end of the lever 15. A knot 23 is then tied near the end of the rope 5, then the rope 5 is pulled back through the hole in the lever 15 until the knot 23 is snugly against the inside surface of the lever 15.

Although depicted on a metal-type hopper-bottomed storage bin, it is not the intention of the inventor to limit the grain sampling device to use on this type of storage bin.

"The embodiments of the invention in which an exclusive property or privilege is claimed are defined as follows:"

We claim:

1. A sampler comprising:

an inclined tube extending through a storage bin wall;

a valve on the inner end of the tube inside the bin;

a rod connected to the valve and mounted slidably inside the tube so as to operate the valve from outside the bin.

2. A sampler for use in grain storage bins comprising:

a push rod and valve assembly inside an inclined tube, the tube extending through the outer vertical wall of a grain storage bin;

a spring affixed to the push rod so as to provide force to close the valve;

a lever that can be caused to push on the push rod with a force sufficient to overcome the closure force exerted by the spring thus opening the valve;

a rope and pulley arrangement that allows an operator to cause the lever to move, the operator being at some distance from the sampling device; and an opening near or at the lower outer end of the tube as a location for collection of a grain sample.

3. A sampler as in claim 2 having the granular sample conveyed, by gravity, in a collection tube to a site convenient to the operator.

4. A sampler as in claim 2 having the sample collected directly under the opening near the lower end of the tube.

5. A sampler as in claim 2 having the push rod and valve assembly operated by the direct manual contact of the operator.

6. A sampler as in claim 2 having an opening near the upper end of the tube that is opened and shut by a closure device.

7. A sampler as in claim 2 having the portion that is inside the storage bin supported by mechanical means.

8. A sampler as in claim 2 that is mounted on the inclined hopper portion of the storage bin so as to extract a sample of granular material from the lower portion of the storage bin.

9. A sampler as in claim 2 having the rod that causes the closure device to open and close as being outside the inclined tube.

* * * * *